United States Patent

Ahmed

(10) Patent No.: US 8,973,754 B2
(45) Date of Patent: Mar. 10, 2015

(54) CASE FOR TOOTH-CLEANING STICK

(71) Applicant: Ishtiaq Ahmed, Toronto (CA)

(72) Inventor: Ishtiaq Ahmed, Toronto (CA)

(73) Assignee: Legeci Inc., Ontario (CA)

( * ) Notice: Subject to any disclaimer, the term of this patent is extended or adjusted under 35 U.S.C. 154(b) by 0 days.

(21) Appl. No.: 13/815,367

(22) Filed: Feb. 26, 2013

(65) Prior Publication Data

US 2013/0284626 A1     Oct. 31, 2013

(51) Int. Cl.
*B65D 83/10* (2006.01)
*A61B 19/02* (2006.01)
*B65D 85/24* (2006.01)
*A61C 19/00* (2006.01)
*A46B 5/00* (2006.01)
*A45D 44/18* (2006.01)

(52) U.S. Cl.
CPC .............. *A61C 19/00* (2013.01); *A46B 5/0041* (2013.01); *A46B 5/005* (2013.01); *A45D 44/18* (2013.01); *A46B 2200/1066* (2013.01)
USPC ............................ 206/368; 132/321; 206/380

(58) Field of Classification Search
USPC ................ 206/37, 37.1, 37.8, 38, 38.1, 63.5, 206/361–362.3, 368, 380–383; 132/321, 132/328, 329; 433/141, 143; D3/205
See application file for complete search history.

(56) References Cited

U.S. PATENT DOCUMENTS

| | | | | |
|---|---|---|---|---|
| 292,059 A | * | 1/1884 | Sackett | 206/380 |
| 469,064 A | * | 2/1892 | McKay | 132/321 |
| 719,017 A | | 1/1903 | Lenhakdtson | |
| 740,586 A | | 10/1903 | Ohlsson | |
| 1,366,092 A | | 1/1921 | Loewenhbkz | |
| 1,509,856 A | | 9/1924 | Williams | |
| 1,559,523 A | | 10/1925 | Waring | |
| 1,640,386 A | | 8/1927 | Wayne | |
| 1,969,874 A | | 8/1934 | Butterfield | |
| 1,983,083 A | | 12/1934 | Irelan | |
| 3,124,399 A | * | 3/1964 | Seta | 206/362.2 |
| 3,127,985 A | * | 4/1964 | Scott | 206/362.3 |
| 3,741,378 A | * | 6/1973 | Parker | 206/361 |
| 4,040,433 A | | 8/1977 | Edison | |
| 4,214,657 A | * | 7/1980 | Winston | 206/362.1 |
| 4,932,547 A | * | 6/1990 | Rodriguez | 206/38 |
| 5,692,609 A | * | 12/1997 | Lin | 206/368 |
| 6,199,695 B1 | * | 3/2001 | Takeo | 206/380 |
| 7,322,765 B2 | | 1/2008 | Wang | |
| 7,665,474 B2 | | 2/2010 | Morales | |
| 7,806,614 B2 | | 10/2010 | Desson | |
| 2009/0229627 A1 | * | 9/2009 | Golden et al. | 132/328 |

* cited by examiner

*Primary Examiner* — Bryon Gehman
(74) *Attorney, Agent, or Firm* — Young & Thompson

(57) ABSTRACT

The case has an inner component which is provided with tweezers for immobilizing an elongated element. The element can be a stick having exposed bristles at one end. The inner component is pivotally attached to an outer component and swings from an open position in which the bristles of the stick are exposed for use as a tooth brush. In the closed position, the stick is entirely within the outer component and is protected by it.

9 Claims, 6 Drawing Sheets

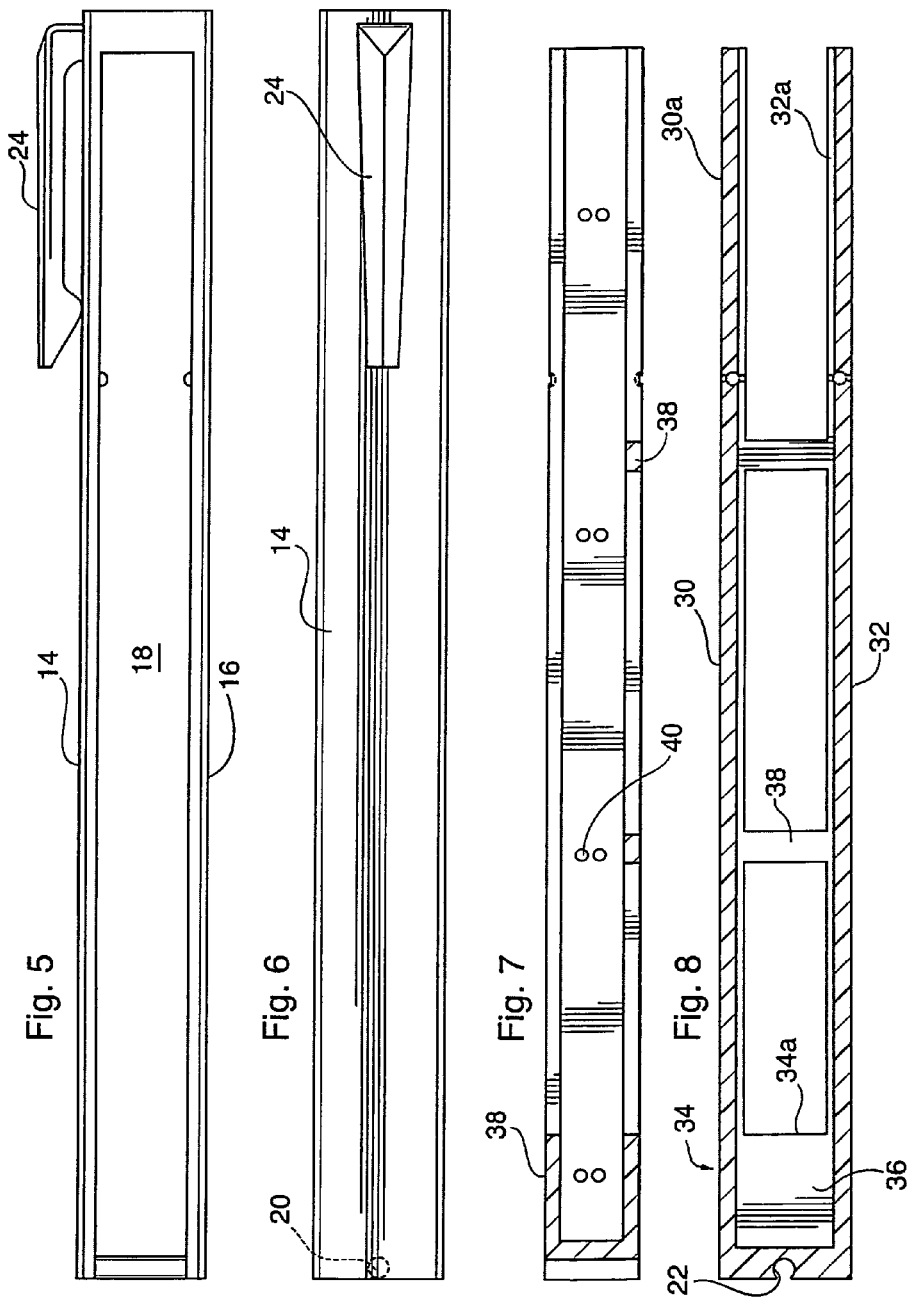

CASE FOR TOOTH-CLEANING STICK

This application claims priority pursuant to 35 USC 119 of Canadian application no. 2,775,495 filed on Apr. 26, 2012 the entire contents of which are hereby incorporated into the following application by reference.

FIELD OF THE INVENTION

This invention relates to brushes for cleaning teeth and more particularly to a case for a teeth-cleaning twig known as a "miswak". A miswak is a twig from a tree known in Arabic as "arak" and sometimes is known as a "peelu". While the case of the invention is intended primarily to hold a miswak, it can hold other things such as dental appliances including small brushes and floss.

BACKGROUND OF THE INVENTION

According to Wikipedia, a miswak has a long, well documented history and is known for its medicinal and hygienic benefits, predominantly in the Arab world. The miswak twig is composed of a number of bristles enclosed in bark. When the bark is removed from the end of the twig, the exposed bristles can be used to brush teeth while the remainder of the twig is held like a toothbrush.

If the twig is not protected in some way between uses, the bristles can break and they can become dirty and unsanitary. The subject invention is directed toward a case for the twig which protects the bristles when the twig is not in use and also doubles as a handle for the twig when it is used as a toothbrush. Not only can the case be used for this purpose but it can also be used to hold other dental appliances such as those mentioned above.

SUMMARY OF THE INVENTION

Briefly, the case of my invention is intended primarily for a stick having oppositely facing inoperative and operative ends, the latter end being adapted to clean teeth. The case includes: inner and outer components, the former having a stick-engaging means for selectively immobilizing the operative end of the stick relative to the inner component. The inner component is pivotal relative to the outer component and swings from an open position in which the operative end of the stick is exposed for use to a closed position in which the operative end of the stick is protected by the outer component.

DESCRIPTION OF THE DRAWINGS

The case of my invention is described with reference to the accompanying drawings in which:

FIG. 5 is an elevation of the outer component of the subject case;

FIG. 6 is an elevation of the outer component rotated 90 degrees from the view illustrated in FIG. 5;

FIG. 7 is an elevation of the inner component of the subject case;

FIG. 8 is an elevation of the inner component rotated 90 degrees from the view illustrated in FIG. 7;

DESCRIPTION OF THE PREFERRED EMBODIMENT

Figure 1:
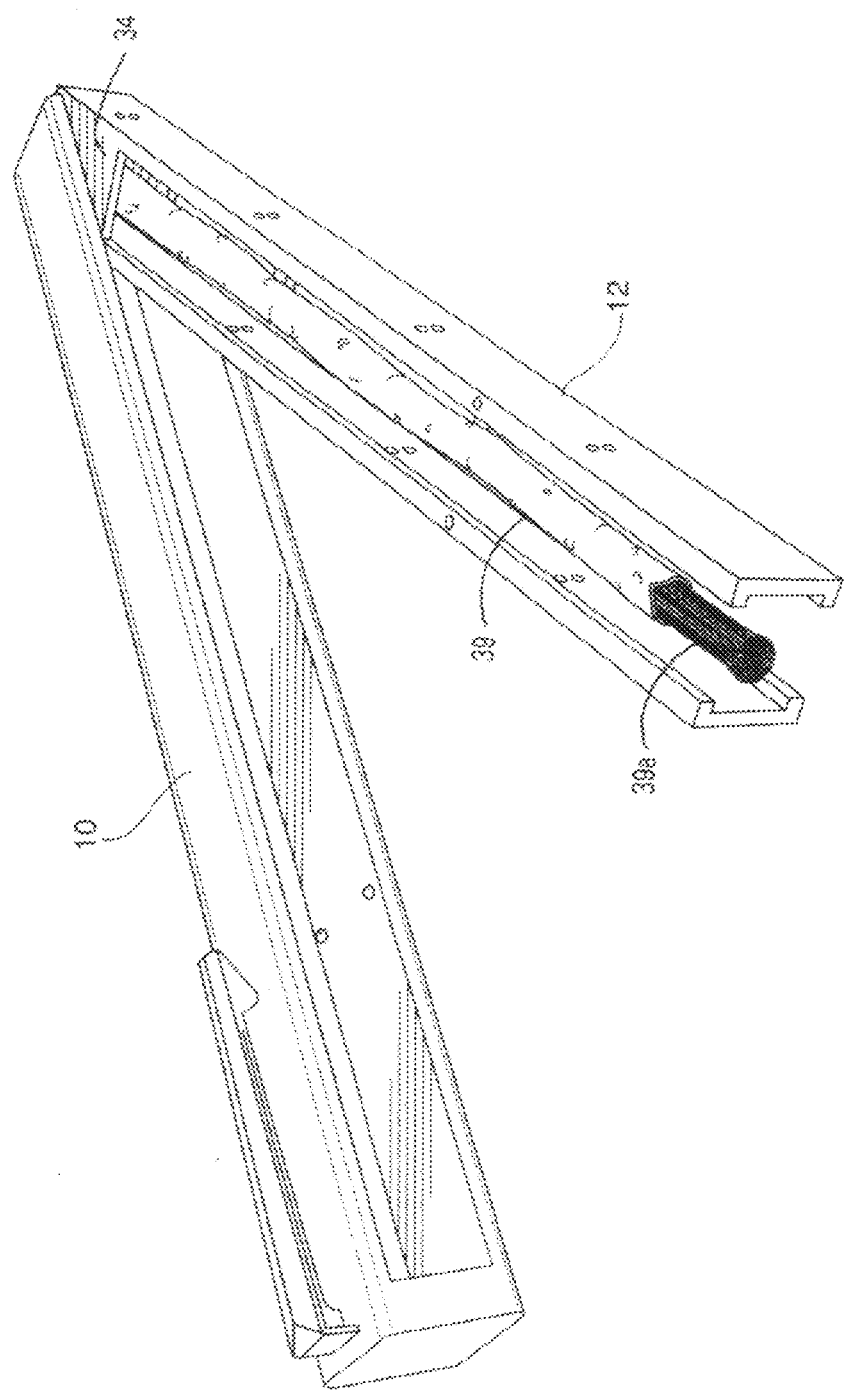
FIG. 1 is a perspective view of the subject case in an open position in conjunction with a miswak twig.
Figure 3:
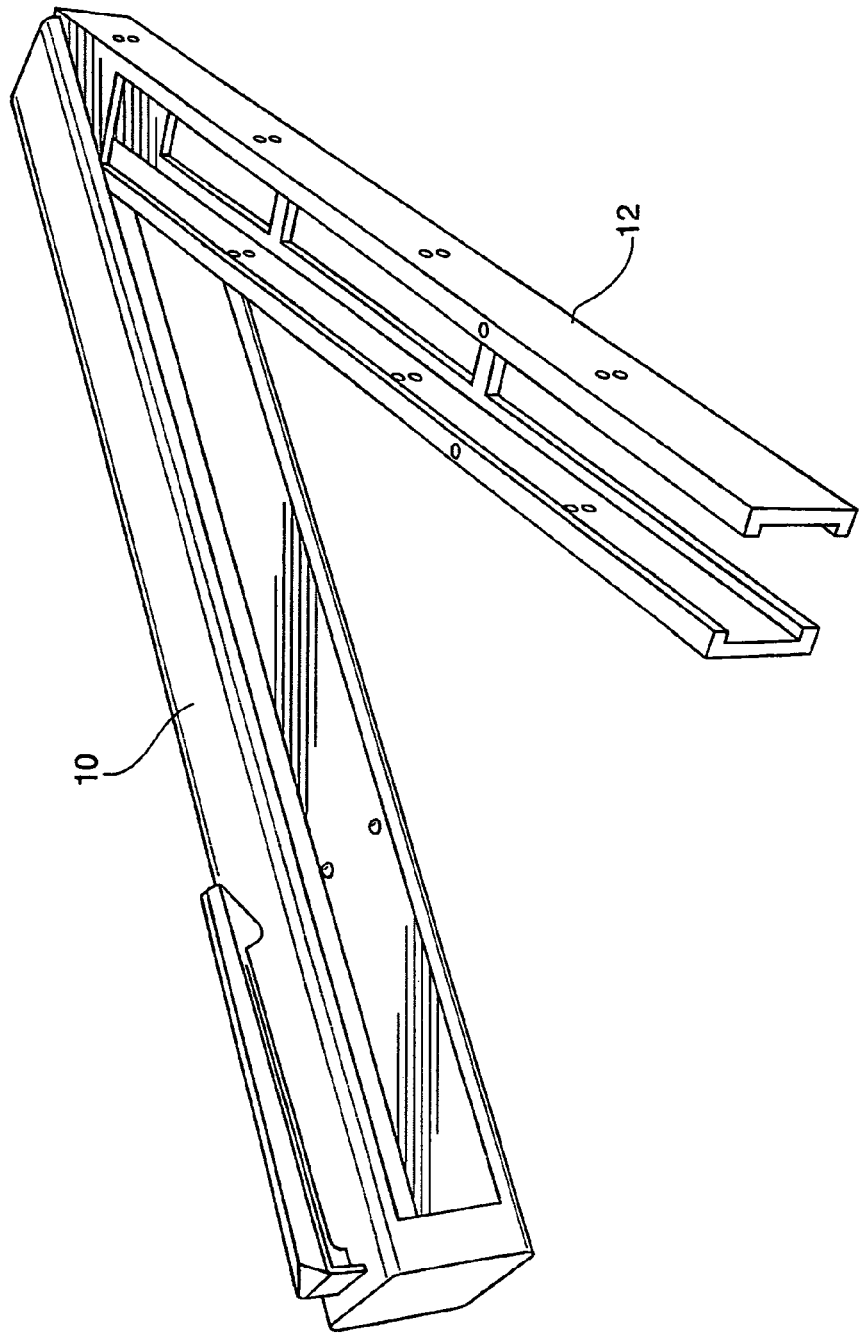
FIG. 3 is a perspective view of the subject case in an open position in the absence of the twig.
Figure 4:
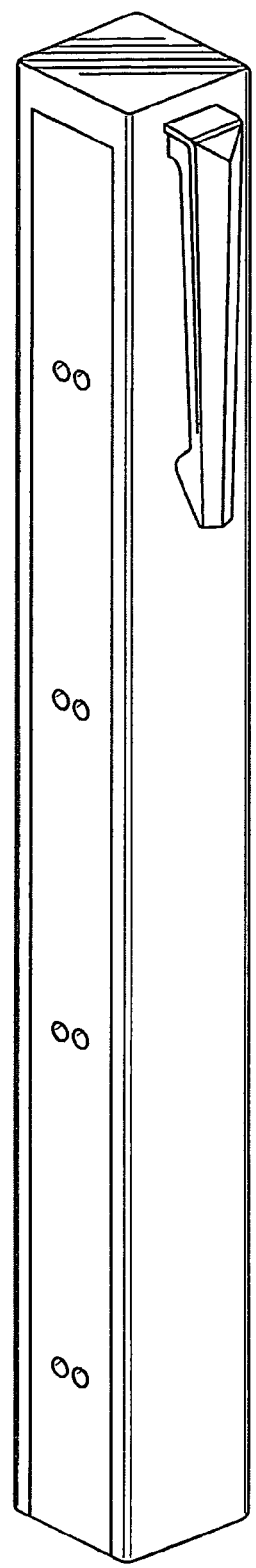
FIG. 4 is an elevation of the subject case closed for storage.

With reference to FIGS. 1, 3, 4 and 5, the case of the invention consists of an outer component 10 and an inner component 12. The outer component is composed of two parallel longitudinally extending outer walls 14, 16 which define an opening 18 in which the inner component is removably received. The two components pivot about a pin 20 at the bottom of the outer component. The pin is accommodated in a conforming groove 22 at the bottom of the inner component as illustrated in FIG. 8. The two components pivot from an open position as illustrated in FIG. 1 in which the inner component is outside the outer component to a closed position in which the inner component is within the outer component as illustrated in FIG. 4.

With reference to FIG. 4, a clip 24 is fastened to outer wall 14 of the outer component so that the subject case, when closed, can be fastened to the upper edge of a pocket in the manner of a fountain pen or a ball point pen. The case itself is cuboid for easy insertion and accommodation in a pocket.

Figure 10:
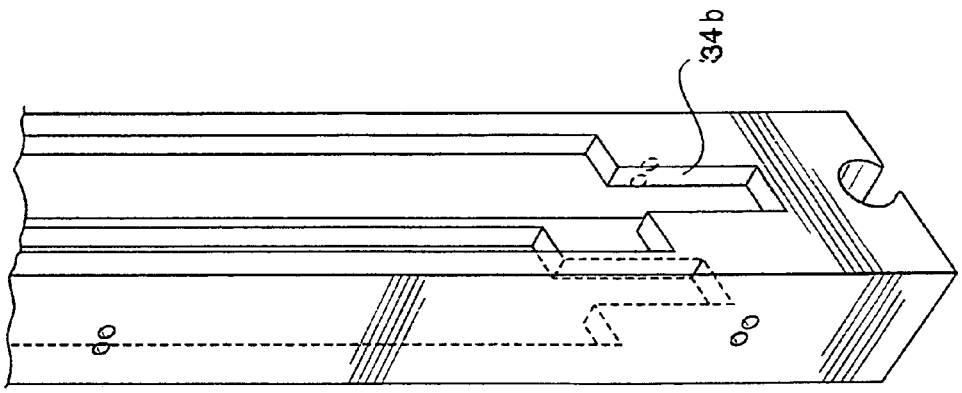
FIG. 10 is a perspective view of a variation of the lower portion of the inner component Like reference characters refer to like parts throughout the description of the drawings.
Figure 9:
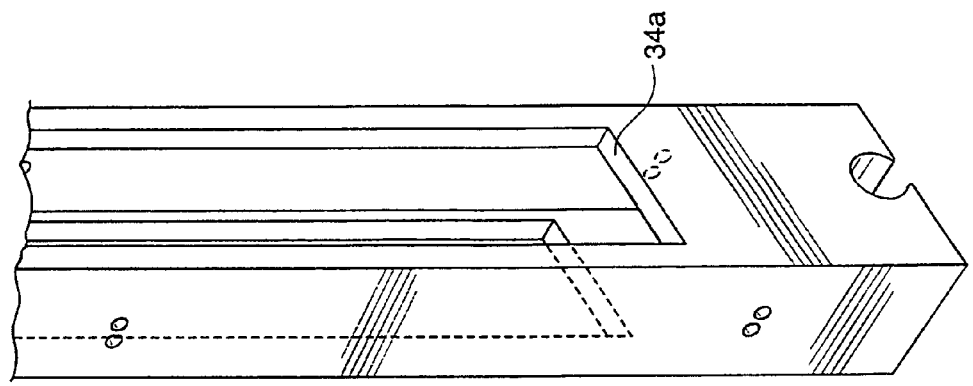
FIG. 9 is a perspective view of the lower portion of the inner component.

With reference to FIGS. 3, 7 and 8, the inner component 12 is composed of two longitudinally extending parallel inner walls 30, 32. The two inner walls at the bottom of the inner component form walls of a compartment, generally 34. The compartment is enclosed by spaced apart side walls 36. The compartment is open at the top and has an upper edge 34a which can be straight as illustrated in FIG. 10 or can have a downwardly extending groove 34b as illustrated in FIG. 9. The groove allows the effective width of side walls 34 to expand to receive a large or irregularly shaped tooth-cleaning stick.

Spaced along the length of the inner walls of the inner component are ribs 38. The ribs serve to hold the two inner walls apart and also to as guides for directing the teeth-cleaning stick in the manner described below. The upper portions 30a, 32a of the two inner walls are resiliently flexible and function as pincers or tweezers for immobilizing the teeth-cleaning stick relative to the inner component when the upper portions are manually pinched as illustrated in FIG. 2.

Figure 2:
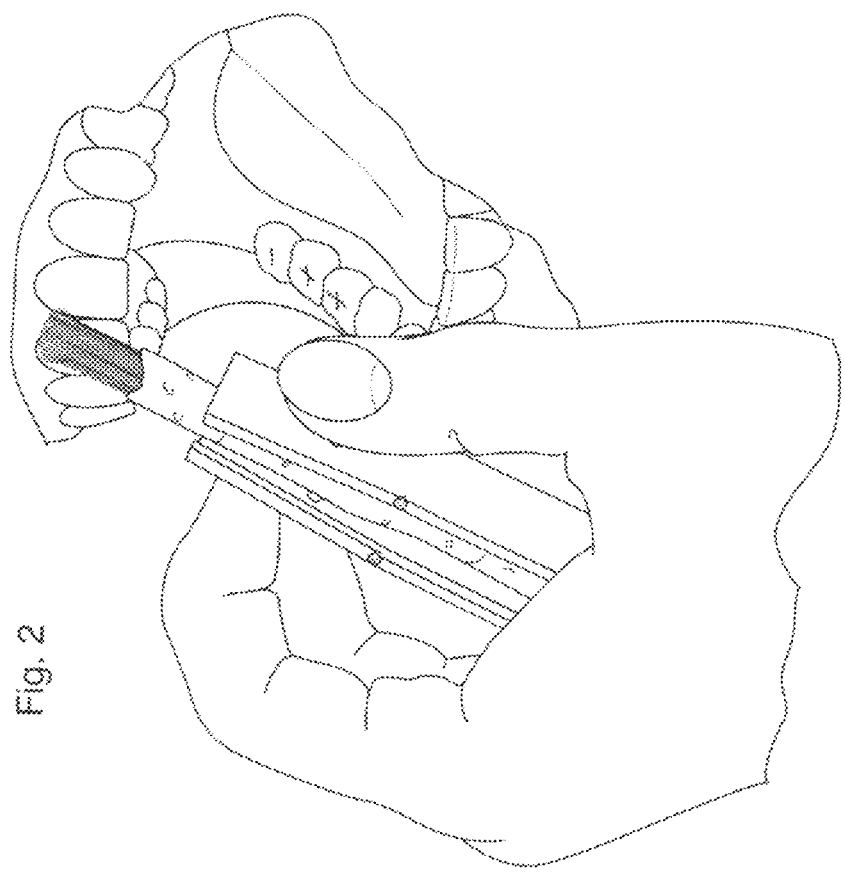
FIG. 2 is a perspective view of the upper portion of the inner component of the subject case and the twig in the process of cleaning teeth.

In use, and with reference to FIGS. 1 and 2, a teeth-cleaning stick 39 is inserted into the space between the inner walls 30, 32 of the inner component. Its lower or inoperative end is received in and hidden by compartment 34 while its upper or operative end 39a protrudes from the stick-engaging means or tweezers 30a, 32a of the inner walls as illustrated in FIG. 2. The bark is removed from the upper end of the stick to expose the bristles.

The salient features of the case of the invention are as follows: (a) when the subject case is open, its inner component is outside the outer component and the operative end of the teeth-cleaning stick is exposed for use while its lower or inoperative end is within compartment 34; (b) the compartment has a rectangular cross-section for ready accommodation of a natural tooth-cleaning stick which typically has an uneven, non-linear shape; (c) the volume of the compartment expands by means of grooves 34b to accommodate such stick; (d) if the stick is not straight, it can be oriented in the compartment so that its operative end is at its most advantageous angle for use in cleaning teeth; and (e) by reason of the pivotal movement of the inner component relative to the outer, the stick can be inserted into the compartment and removed from it without difficulty so that the stick can be removed from the case of the invention or inserted into it while the case remains in a pocket or wherever else it is being carried.

An anti-bacterial sponge can be inserted in compartment 34 to absorb any drips from the bristles and to inhibit bacterial growth. The case has a flat bottom wall so that it can be stored upright. Moisture left on the stick after use will accordingly run downwardly into the sponge. Vent holes 40 are provided in the inner walls of the inner component to further inhibit bacterial growth within the subject case when it is closed.

Ribs 38 function not only to strengthen the inner walls of the inner component but to guide the stick toward the stick engaging means when the stick is being inserted into the inner component. When the inner component is closed as illustrated in FIG. 4, the operative end of the stick is protected from contamination by dirt and from breakage.

It will be understood, of course, that modifications can be made in the structure of the case of the invention without departing from the scope and purview of the invention as defined in the appended claims.

I claim:

1. A case for a stick, the stick having oppositely facing operative and inoperative ends, the operative end adapted to clean teeth, said case including: an inner component and an outer component, said inner component being pivotal relative to said outer component and pivoting from an open position in which the operative end of the stick is adapted to be exposed for use to a closed position in which the operative end of the stick is adapted to be protected by said outer component, said inner component further having a pair of longitudinally extending spaced inner walls between which the entire stick is adapted to be accommodated, said inner walls each defining a free end and being resiliently flexible which, when the stick is extended longitudinally out from between the inner walls and the inner walls are manually pinched, the free ends will approach each other resulting in the free ends engaging the extended stick to immobilize the stick relative to said inner component such that the operative end protrudes outward from said inner to be used to clean teeth while the remainder of the stick remains between said inner walls.

2. The case as claimed in claim 1 further including a separate compartment in which the inoperative end of the stick is adapted to be removably accommodated.

3. The case of claim 2 further including a guide for directing the inoperative end of the stick toward said compartment when the stick is being inserted into the inner component.

4. The case of claim 2 wherein said compartment has opposite sides each having a groove formed therein for the effective enlargement of the width of the space between said opposite sides with resulting engagement of the volume of said compartment.

5. The case of claim 2 wherein a plurality of vent holes are provided in said inner walls of said inner component to minimize the build-up of moisture within said inner walls.

6. The case of claim 2 further including an antibacterial sponge disposed within said compartment.

7. The case of claim 1 wherein said outer component has a pair of longitudinally extending outer walls between which said inner component is accommodated when said inner component is in said closed position.

8. The case of claim 1 wherein said outer component is cuboid.

9. The case of claim 1 wherein said outer component has a flat bottom wall so that said outer component can be stored upright.

* * * * *